United States Patent
Konishi et al.

(10) Patent No.: US 11,419,796 B2
(45) Date of Patent: Aug. 23, 2022

(54) STICK-SHAPED COSMETIC PRODUCT

(71) Applicant: SHIN-ETSU CHEMICAL CO., LTD., Tokyo (JP)

(72) Inventors: Masayuki Konishi, Tokyo (JP); Chihiro Hayakawa, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 242 days.

(21) Appl. No.: 16/087,509

(22) PCT Filed: Mar. 7, 2017

(86) PCT No.: PCT/JP2017/008989
§ 371 (c)(1),
(2) Date: Sep. 21, 2018

(87) PCT Pub. No.: WO2017/163854
PCT Pub. Date: Sep. 28, 2017

(65) Prior Publication Data
US 2019/0099333 A1     Apr. 4, 2019

(30) Foreign Application Priority Data

Mar. 22, 2016  (JP) .............................. JP2016-056775

(51) Int. Cl.
| | | |
|---|---|---|
| A61K 8/02 | (2006.01) | |
| A61K 8/31 | (2006.01) | |
| A61K 8/34 | (2006.01) | |
| A61K 8/892 | (2006.01) | |
| A61K 8/894 | (2006.01) | |
| A61Q 19/00 | (2006.01) | |
| A61K 8/92 | (2006.01) | |
| A61K 8/893 | (2006.01) | |
| A61K 8/81 | (2006.01) | |
| A61Q 1/02 | (2006.01) | |
| A61Q 19/08 | (2006.01) | |
| A61K 8/06 | (2006.01) | |

(52) U.S. Cl.
CPC ............. *A61K 8/0229* (2013.01); *A61K 8/31* (2013.01); *A61K 8/34* (2013.01); *A61K 8/345* (2013.01); *A61K 8/8111* (2013.01); *A61K 8/892* (2013.01); *A61K 8/893* (2013.01); *A61K 8/894* (2013.01); *A61K 8/922* (2013.01); *A61K 8/927* (2013.01); *A61Q 1/02* (2013.01); *A61Q 19/00* (2013.01); *A61Q 19/007* (2013.01); *A61Q 19/08* (2013.01); *A61K 8/064* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 2013/0272995 A1* | 10/2013 | Hagiwara | ............. C08F 230/08 424/78.35 |
| 2014/0328779 A1 | 11/2014 | Hagiwara et al. | |
| 2017/0266082 A1 | 9/2017 | Matsufuji et al. | |

FOREIGN PATENT DOCUMENTS

| | | |
|---|---|---|
| JP | 11-92335 A | 4/1999 |
| JP | 2003-63919 A | 3/2003 |
| JP | 2004-137212 A | 5/2004 |
| JP | 2008-247773 A | 10/2008 |
| JP | 2012-211103 A | 11/2012 |
| JP | 2013-221028 A | 10/2013 |
| JP | 2015-218113 A | 12/2015 |

OTHER PUBLICATIONS

Extended European Search Report dated Sep. 26, 2019, in European Patent Application No. 17769899.0.
Shin Etsu: "Shin Etsu Unique Materials. Silicone Products for Personal Care," Internet Citation, Feb. 1, 2008 (Feb. 1, 2008), p. 20pp, XP007906619, Retrieved from the Internet: URL:http://www.shinetsusilicones.com/SESA%20Personal%20Care%20Unique%20Material.pdf [retrieved on 1077]. pp. 8-11.
International Search Report, issued in PCT/JP2017/008989, dated Apr. 25, 2017.
Written Opinion of the International Searching Authority, issued in PCT/JP2017/008989, dated Apr. 25, 2017.

\* cited by examiner

*Primary Examiner* — Nicole P Babson
(74) *Attorney, Agent, or Firm* — Birch, Stewart, Kolasch & Birch, LLP

(57) ABSTRACT

A stick-shaped cosmetic product including (a) 0.1 to 4 mass % of at least one selected from a partially cross-linked polyether modified silicone and a partially cross-linked polyglycerin modified silicone, (b) 1 to 10 mass % of wax, and (c) 30 mass % or more of an aqueous component.

9 Claims, No Drawings

STICK-SHAPED COSMETIC PRODUCT

TECHNICAL FIELD

This invention relates to a stick-shaped cosmetic composition. It is noted that a composition for cosmetic formulation is sometimes described as cosmetic.

BACKGROUND ART

In general, cosmetics serving as means for moisturizing dry skin include serum or concentrate and cream. Such cosmetics, however, lack convenience in that when they are applied to the skin, they must be once took in the hand and rubbed to the face or intended site. While misting cosmetics which are applicable without a need for hand transfer are known, they suffer other problems such as clogging due to viscosity, spraying to an unintended site, and suction.

On the other hand, stick-shaped cosmetics can be applied to the intended site without a need to take in the hand before coating. The stick-shaped cosmetics to be applied to the skin include oily stick-shaped cosmetics, which suffer from problems like sticking and glittering. The technique for controlling such problems by powder formulation is known from Patent Document 1: JP-A 2008-247773. However, sticky feel reduction is insufficient as moisturizing cosmetics. The technique of aqueous stick-shaped cosmetics is known from Patent Document 2: JP-A 2004-137212, but it lacks a sustaining or emollient effect because an oily component cannot be fully blended.

Besides, the technology of stick-shaped emulsion cosmetics is known from Patent Document 3: JP-A 2015-218113. However, the silicone elastomers used therein such as (diphenyl dimethicone/vinyldiphenyl dimethicone/silsesquioxane) crosspolymers are not effective for swelling and achieve an insufficient improvement in formulation stability.

PRIOR ART DOCUMENTS

Patent Documents

Patent Document 1: JP-A 2008-247773
Patent Document 2: JP-A 2004-137212
Patent Document 3: JP-A 2015-218113

SUMMARY OF INVENTION

Technical Problem

An object of the invention, which has been made under the above-mentioned circumstances, is to provide a stick-shaped cosmetic composition featuring unbreakableness from stick shape, a pleasant feeling on use without stickiness, an excellent moisturizing and emollient effect, persistence thereof, ease of spreading, formulation stability during storage, and ease of filling into a stick container.

Solution to Problem

Making extensive investigations to attain the above object, the inventors have found that the outstanding problems are overcome by a cosmetic composition comprising specific amounts of (a) at least one member selected from a partially crosslinked polyether-modified silicone and a partially crosslinked polyglycerol-modified silicone, (b) a wax, and (c) an aqueous component. The invention is predicated on this finding.

Advantageous Effects of Invention

The invention provides provide a stick-shaped cosmetic composition having advantages including unbreakableness from stick shape, a pleasant feeling on use without stickiness, an excellent moisturizing and emollient effect, persistence thereof, ease of spreading, formulation stability during storage, and ease of filling into a stick container (or smooth flow at high temperature).

DESCRIPTION OF EMBODIMENTS

Several embodiments of the invention are described below in detail although the invention is not limited thereto.

Component (a)

Component (a) is at least one silicone selected from a partially crosslinked polyether-modified silicone and a partially crosslinked polyglycerol-modified silicone.

The partially crosslinked polyether-modified silicone is not particularly limited as long as it has a three-dimensional crosslinked structure in which organopolysiloxane chains are crosslinked with polyether. Examples of the partially crosslinked polyether-modified silicone include (dimethicone/(PEG-10/15)) crosspolymer, (PEG-15/lauryl dimethicone) crosspolymer, and (PEG-15/laurylpolydimethylsiloxyethyl dimethicone) crosspolymer, as expressed according to the nomenclature of cosmetic ingredients. These substances are commercially available as swollen products containing silicone oil or another oil, and marketed, for example, under the trade name of KSG-210, 240, 310, 340, and 320Z (all from Shin-Etsu Chemical Co., Ltd.).

The partially crosslinked polyglycerol-modified silicone is not particularly limited as long as it has a three-dimensional crosslinked structure in which organopolysiloxane chains are crosslinked with polyglycerol. Examples of the partially crosslinked polyglycerol-modified silicone include (dimethicone/polyglycerol-3) crosspolymer, (lauryl dimethicone/polyglycerol-3) crosspolymer, and (polyglycerol-3/laurylpolydimethylsiloxyethyl dimethicone) crosspolymer, as expressed according to the nomenclature of cosmetic ingredients. These substances are commercially available as swollen products containing silicone oil or another oil, and marketed, for example, under the trade name of KSG-710, 810, 820Z, and 840 (all from Shin-Etsu Chemical Co., Ltd.).

The amount of component (a) blended is 0.1 to 4% by weight, preferably 0.2 to 2% by weight of the total weight of the stick-shaped cosmetic composition. Less than 0.1% by weight of component (a) may result in a cosmetic composition with low emulsion stability whereas more than 4% by weight of component (a) may interfere with freshness and impair a feeling on use upon rubbing.

Component (a) may be used alone or in suitable combination of two or more. For example, with respect to the combination of a partially crosslinked polyether-modified silicone and a partially crosslinked polyglycerol-modified silicone, a relatively high blend ratio of the partially crosslinked polyether-modified silicone has the tendency that the cosmetic composition is effectively spread, whereas a relatively high blend ratio of the partially crosslinked polyglycerol-modified silicone has the tendency that the cosmetic composition presents an emollient and soft feeling on use. The blend ratio may be determined as appropriate depending on the degree of control of feeling on use.

Component (b)

Component (b) is a wax which is not particularly limited as long as it can be formulated in ordinary cosmetic compositions. Examples include ceresin, ozokerite, microcrystalline wax, synthetic hydrocarbon waxes such as polyethylene wax, vegetable waxes such as carnauba wax, rice wax, rice bran wax, jojoba wax (including extremely hydrogenated jojoba wax) and candelilla wax, and animal waxes such as beeswax. These waxes may be used alone or in admixture of two or more.

Component (b) preferably has a melting point of at least 60° C. Examples include ceresin, polyethylene and synthetic waxes. The wax component contains preferably at least 70% by weight, more preferably at least 80% by weight of a wax having a melting point of at least 60° C. If the content of a wax having a melting point of at least 60° C. is less than 70% by weight, there arises the risk of difficult molding to stick shape.

The amount of component (b) blended is 1 to 10% by weight, preferably 3 to 8% by weight of the total weight of the stick-shaped cosmetic composition. A composition with less than 1% by weight of component (b) may have too low a hardness to maintain stick shape whereas a composition with more than 10% by weight of component (b) may have too high a hardness to apply and give an unpleasant feeling on use.

Component (c)

Component (c) used herein is an aqueous component which is not particularly limited as long as it can be formulated in ordinary cosmetic compositions. Examples include water, moisturizers and humectants, which may be used alone or in admixture of two or more.

Examples of water include purified water as commonly used in cosmetics and sea water, spring water, peat water and distilled water from fruits or vegetables.

Suitable moisturizers include lower alcohols such as ethanol and isopropanol; sugar alcohols such as sorbitol, maltose and xylitol; polyhydric alcohols such as butylene glycol, dibutylene glycol, propylene glycol, pentylene glycol, decane diol, octane diol, hexane diol, erythritol, glycerol, diglycerol, and polyethylene glycol; glucose, glyceryl glucoside, betaine, hyaluronic acid, chondroitin sulfate, pyrrolidone carboxylate, polyoxyethylene methyl glucoside, and polyoxypropylene methyl glucoside.

The amount of component (c) blended is at least 30% by weight, preferably at least 50% by weight, more preferably at least 60% by weight of the total weight of the stick-shaped cosmetic composition. The upper limit is up to 90% by weight though not critical.

More particularly, the amount of water blended is preferably 5 to 70% by weight of the total weight of the stick-shaped cosmetic composition. Also the amount of moisturizer blended is preferably 5 to 70% by weight of the total weight of the stick-shaped cosmetic composition. Less than 5% by weight may be difficult to exert a satisfactory moisturizing effect and adversely affect formulation stability whereas more than 70% by weight may render the composition sticky and detract from the feeling on use.

Component (d)

In the stick-shaped cosmetic composition, (d) a partially crosslinked organopolysiloxane having an alkyl branched chain in its backbone is preferably blended from the standpoints of formulation stability during storage and ease of filling in a stick container. The partially crosslinked organopolysiloxane having an alkyl branched chain in its backbone is not particularly limited as long as it can be formulated in ordinary cosmetic compositions, and may be used alone or in admixture of two or more. Unlike component (a), component (d) is a compound free of a polyether or polyglycerol structure in its molecule, that is, an elastomer which exhibits a structural viscosity when swollen with oil. Examples include (vinyl dimethicone/lauryl dimethicone) crosspolymer, and (lauryl polydimethylsiloxyethyl dimethicone/bisvinyl dimethicone) crosspolymer, as expressed according to the nomenclature of cosmetic ingredients. These substances are commercially available as swollen products containing oil which is liquid at room temperature, and include, for example, KSG-41A, 42A, 43, 44, 042Z, 045Z and 048Z (all from Shin-Etsu Chemical Co., Ltd.).

When used, the amount of component (d) blended is preferably 0.1 to 4% by weight, more preferably 0.2 to 2% by weight of the total weight of the stick-shaped cosmetic composition. At least 0.1% by weight of component (d) further improves the emulsion stability of a cosmetic composition whereas up to 4% by weight of component (d) improves freshness and feeling on use upon application.

Component (e)

In the stick-shaped cosmetic composition, (e) a non-crosslinked silicone active agent is preferably blended from the standpoint of formulation stability during storage. The non-crosslinked silicone active agent is not particularly limited as long as it can be formulated in ordinary cosmetic compositions, and may be used alone or in admixture of two or more. Preferred among these surface active agents are linear or branched polyoxyethylene-modified organopolysiloxane such as PEG-9 polydimethylsiloxyethyl dimethicone (as expressed according to the nomenclature of cosmetic ingredients), linear or branched polyoxyethylene polyoxypropylene-modified organopolysiloxane, linear or branched polyoxyethylene/alkyl co-modified organopolysiloxane, linear or branched polyoxyethylene polyoxypropylene/alkyl co-modified organopolysiloxane, linear or branched polyglycerol-modified organopolysiloxane, and linear or branched polyglycerol/alkyl co-modified organopolysiloxane. Specific examples include KF-6011, 6013, 6043, 6017, 6028, 6038, 6048, 6100, 6104, 6105, and 6106. These non-crosslinked silicone active agents may be used alone or in admixture of two or more.

When used, the amount of component (e) blended is preferably 0.1 to 2% by weight, more preferably 0.2 to 0.8% by weight of the total weight of the stick-shaped cosmetic composition. At least 0.1% by weight of component (e) further improves the emulsion stability of a cosmetic composition whereas up to 2% by weight of component (e) provides freshness and a pleasant feeling on use upon application.

Component (f)

By blending a silicone powder in the stick-shaped cosmetic composition, it becomes possible to impart a morphological correcting effect to the skin, to impart a fresh feeling on use, and to suppress sticky feeling due to wax. The silicone powder is a powder having siloxane bonds, and examples thereof include crosslinked silicone powder (i.e., so-called silicone rubber powder composed of organopolysiloxane having a structure in which repeating chains of diorganosiloxane units are crosslinked) and silicone resin particles (polyorganosilsesquioxane resin particles of three dimensional network structure). Specific examples include (dimethicone/vinyl dimethicone) crosspolymer, and polymethylsilsesquioxane, as expressed according to the nomenclature of cosmetic ingredients. They are commercially available in powder form or as swollen products containing silicone oil and marketed, for example, under the trade name of KMP-598, 590, 591, and KSG-016F (all from Shin-Etsu Chemical Co., Ltd.). They may be used alone or in admixture of two or more.

In particular, silicone resin-coated silicone rubber powder is applied in sunscreen, make-up and concealer products because of its feel-improving effect (sticky feel prevention), and morphological correcting effect for wrinkles and pores. Examples of the silicone resin-coated silicone rubber powder include (vinyl dimethicone/methicone silsesquioxane) crosspolymer, (diphenyl dimethicone/vinyldiphenyl dimethicone/silsesquioxane) crosspolymer, polysilicone-22, and polysilicone-1 crosspolymer, as expressed according to the nomenclature of cosmetic ingredients. These powders are marketed, for example, under the trade name of KSP-100, 101, 105, 300, 411, and 441 (all from Shin-Etsu Chemical Co., Ltd.). They may be used alone or in admixture of two or more.

Component (f) preferably has an average primary particle size of less than 15 µm, more preferably less than 7 µm. If a silicone powder with an average primary particle size to of 15 µm or more is blended in a large fraction, then the resulting stick is easy to break. Further, particles with spherical shape and a diameter approximate to a sphere, i.e., spherical particles are preferred. Specifically, a powder of spherical particles with a breadth/length ratio of up to 1.5/1, more preferably up to 1.2/1, even more preferably up to 1.1/1 is desirable.

The preferred component (f) is a powder which is unlikely to absorb an oil which is liquid at room temperature in the cosmetic composition. Preference is given to a powder which absorbs an oil phase which is liquid at room temperature in the cosmetic composition in an amount of less than 150 mL/100 g, more preferably less than 100 mL/100 g, in the measurement of oil absorption according to JIS K5101. If a powder having an oil absorption of 150 mL/100 g or more is blended in a large fraction, then the resulting stick is easy to break.

When used, the amount of component (f) blended is preferably 0.1 to 5% by weight, more preferably 1 to 3% by weight of the total weight of the stick-shaped cosmetic composition. At least 0.1% by weight of component (f) provides more freshness and morphological correcting effect whereas more than 5% by weight of component (f) leads to the tendency that the resulting stick is easy to break.

In the cosmetic composition of the invention, various components which are used in ordinary cosmetic compositions may be blended as long as the benefits of the invention are not impaired. Such components include, for example, (1) oil, (2) powder other than component (f), (3) composition consisting of a crosslinked organopolysiloxane and an oil which is liquid at room temperature, (4) film-forming agent, (5) surfactant, and (6) other arbitrary additives, each of which may be used alone or in admixture. These components are properly selected and used depending on the type of cosmetics, and their amounts blended may be any well-known amounts depending on the type of cosmetics.

(1) Oil

Oils may be solid, semi-solid or liquid at room temperature. Examples of the oil used herein include silicone oils, natural animal and vegetable oils and fats, semi-synthetic oils and fats, hydrocarbon oils, higher alcohols, fatty acids, ester oils, and fluorochemical oils. When used, the amount of the oil blended is preferably 5 to 65% by weight, more preferably 15 to 40% by weight of the total weight of the stick-shaped cosmetic composition.

Silicone Oil

The silicone oils used herein are not particularly limited as long as they can be blended in ordinary cosmetic compositions. Examples include linear or branched organopolysiloxanes ranging from low viscosity to high viscosity such as dimethylpolysiloxane, cyclopentasiloxane, cyclohexasiloxane, disiloxane, trisiloxane, methyl trimethicone, caprylyl methicone, methylphenylpolysiloxane, methylhexylpolysiloxane, methylhydrogenpolysiloxane, dimethylsiloxane/methylphenylsiloxane copolymers; silicone rubbers such as amino-modified organopolysiloxane, pyrrolidone-modified organopolysiloxane, pyrrolidonecarboxylic acid-modified organopolysiloxane, gum-like dimethylpolysiloxane having a high degree of polymerization, gum-like amino-modified organopolysiloxane, gum-like dimethylsiloxane/methylphenylsiloxane copolymers; cyclic organopolysiloxane solution of silicone gum or rubber, trimethylsiloxysilicic acid, cyclic siloxane solution of trimethylsiloxysilicid acid, higher alkoxy-modified silicone such as stearoxysilicone, higher fatty acid-modified silicone, alkyl-modified silicone, long chain alkyl-modified silicone, amino acid-modified silicone, fluorine-modified silicone, silicone resins and silicone resin solutions.

Among others, volatile silicone which gives a light feeling on use (commercially available as TMF-1.5, KF-995, KF-96A-2cs, KF-96A-6cs from Shin-Etsu Chemical Co., Ltd.), phenylsilicone used for the purposes of improving compatibility with other oils and lustering (commercially available as KF-56A (diphenylsiloxyphenyl trimethicone) and 54HV from Shin-Etsu Chemical Co., Ltd.), and silicone wax used for the purposes of lustering and adjusting feeling on use (commercially available as KP-561P, 562P, KF-7020S from Shin-Etsu Chemical Co., Ltd.) are preferably utilized. These silicone oils may be used alone or in admixture. The amount of the silicone oil blended is preferably 5 to 65% by weight, more preferably 15 to 40% by weight of the total weight of the stick-shaped cosmetic composition.

(2) Powder Other Than Component (f)

The powder used herein is not particularly limited as long as it can be blended in ordinary cosmetic compositions. A pigment is typical. The pigment used herein is not particularly limited as long as it is commonly used in make-up cosmetic compositions. Examples include inorganic pigments such as talc, mica, kaolin, silica, calcium carbonate, zinc white, titanium dioxide, red iron oxide, yellow iron oxide, black iron oxide, ultramarine, Prussian blue, carbon black, low order titanium oxide, cobalt violet, chromium oxide, chromium hydroxide, cobalt titanate, bismuth oxychloride, titanium-mica base pearl pigment; organic pigments in the form of zirconium, barium or aluminum lake such as Red #201, Red #202, Red #204, Red #205, Red #220, Red #226, Red #228, Red #405, Orange #203, Yellow #205, Yellow #4, Yellow #5, Blue #1, Blue #404, and Green #3; natural colorants such as chlorophyll and β-carotene; and dyes. Also those pigments which have been treated with silicone or the like to be hydrophobic may be used.

(3) Composition Consisting of a Crosslinked Organopolysiloxane and an Oil Which is Liquid at Room Temperature Any crosslinked organopolysiloxanes other than components (a) and (d) defined above may be used. In the composition consisting of a crosslinked organopolysiloxane and an oil which is liquid at room temperature, the crosslinked organopolysiloxane is preferably swollen by containing the liquid oil in an amount of equal to or more than its own weight. Examples of the liquid oil used herein include liquid silicone oil, hydrocarbon oil, ester oil, natural animal and vegetable oils, semi-synthetic oil, and fluorochemical oil listed above as component (1). For example, silicone oil having a low viscosity of 0.65 to 100 mm$^2$/s at 25° C., liquid paraffin, squalane, hydrocarbon oils such as isododecane and isohexadecane, glyceride oil such as triethylhexanoin, ester oils such as isotridecyl isononanoate, N-acylglutamic acid esters, lauroyl sarcosine acid esters, and natural animal and vegetable oils such as macadamia nut oil. Examples include KSG-15, 1510, 16, 15AP, 0, 18A, and 19 from Shin-Etsu Chemical Co., Ltd.

(4) Film-Forming Agent

The film-forming agent used herein is not particularly limited as long as it is commonly used in cosmetics. Examples include latexes such as polyvinyl alcohol, polyvinyl pyrrolidone, polyvinyl acetate, polyalkyl acrylates; cellulose derivatives such as dextrin, alkyl celluloses, and nitrocellulose; silicone-modified polysaccharides such as pullulan tri(trimethylsiloxy)silylpropylcarbamate, acrylic silicone base graft copolymers such as (alkyl acrylate/dimethicone) copolymers, silicone resins such as trimethylsiloxysilicic acid, silicone base resins such as silicone-modified polynorbornene and fluorine-modified silicone resins, fluoro-resins, aromatic hydrocarbon resins, polymer emulsion resins, terpene resins, polybutene, polyisoprene, alkyd resins, polyvinyl pyrrolidone-modified polymers, rosin-modified resins, and polyurethane.

Among these, silicone base film-forming agents are preferred. More preferred examples include, but are not limited to, pullulan tri(trimethylsiloxy)silylpropylcarbamate (commercially available in solvent solution form as TSPL-30-D5, ID from Shin-Etsu Chemical Co., Ltd.), (alkyl acrylate/dimethicone) copolymers (commercially available in solvent solution form as KP-543, 545, 549, 550, 545L from Shin-Etsu Chemical Co., Ltd.), trimethylsiloxysilicic acid (commercially available in solvent solution form as KF-7312J, X-21-5250 from Shin-Etsu Chemical Co., Ltd.), and silicone-modified polynorbornene (commercially available in solvent solution form as NBN-30-ID from Shin-Etsu Chemical Co., Ltd.). The film-forming agent may be used alone or in admixture.

(5) Surfactant

Any surfactants other than components (a) and (e) defined above may be used. Suitable surfactants include nonionic, anionic, cationic and ampholytic surfactants. The surfactant is not particularly limited, and any surfactant may be selected as long as it is commonly used in cosmetics.

(6) Other Arbitrary Additives

Other additives include oil-soluble gelling agents, antiperspirants, UV absorbers, moisturizers, preservatives, bactericides, perfumes, salts, antioxidants, pH adjusting agents, chelating agents, refreshing agents, anti-inflammatory agents, skin improving agents (brightening agent, cell activating agent, anti-skin-roughening agent, blood flow promotor, skin astringent, antiseborrheic agent), vitamins, amino acids, water-soluble polymers, and inclusion compounds.

Oil-soluble Gelling Agent

Suitable oil-soluble gelling agents include metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organo-modified clay minerals such as disteardimonium hectorite, stearalkonium hectorite and hectorite.

Antiperspirant

Suitable antiperspirants include aluminum chlorohydrate, aluminum chloride, aluminum sesquichlorohydrate, zirconium hydroxychloride, aluminum zirconium hydroxychloride, and aluminum zirconium glycine complex.

UV Absorber

Suitable UV absorbers include homomenthyl salicylate, octocrylene, 4-tert-butyl-4'-methoxydibenzoylmethane, 4-(2-β-glucopyranosiloxy)propoxy-2-hydroxybenzophenone, octyl salicylate, hexyl 2-[4-(diethylamino)-2-hydroxybenzoyl]benzoate, dihydroxydimethoxybenzophenone, sodium dihydroxydimethoxybenzophenonedisulfonate, dihydroxybenzophenone, dimethicodiethylbenzal malonate, 1-(3,4-dimethoxyphenyl)-4,4-dimethyl-1,3-pentanedione, 2-ethylhexyl dimethoxybenzylidenedioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methylbis (trimethylsiloxy)silylisopentyl trimethoxycinnamate, drometrizole trisiloxane, 2-ethylhexyl p-dimethylaminobenzoate, isopropyl p-methoxycinnamate, 2-ethylhexyl p-methoxycinnamate, 2,4-bis[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenone sulfonic acid and trihydrate thereof, sodium hydroxymethoxybenzophenone sulfonate, phenylbenzimidazole sulfonic acid, and 2,2'-methylenebis(6-(2H-benzotriazol-2-yl)-4-(1,1,3,3-tetramethylbutyl)phenol).

Also, a UVA absorber (e.g., hexyl diethylaminohydroxybenzoylbenzoate) may be combined with a UVB absorber (e.g., ethylhexyl methoxycinnamate).

Preservative and Bactericide

Examples of the preservative and bactericide include alkyl p-hydroxybenzoates, benzoic acid, sodium benzoate, sorbic acid, potassium sorbate, phenoxyethanol, imidazolidinium urea, salicylic acid, isopropyl methyl phenol, carbolic acid, alkyl p-hydroxybenzoates, p-chloro-m-cresol, hexachlorophene, benzalkonium chloride, chlorohexidine chloride, trichlorocarbaniride, iodopropinyl butylcarbamate, polylysine, photosensitizer, silver, and plant extracts.

The stick-shaped cosmetic composition of the invention is obtainable by heat mixing oily components to form a mixture, adding an aqueous component to the heated mixture, emulsifying, filling a stick container or mold with the emulsion, and slowly cooling.

The state of the cosmetic composition is not particularly limited as long as it is of stick shape. The emulsion form may be either W/O or O/W/O type emulsion.

Rheometer Hardness

The cosmetic composition of the invention should have a sufficient hardness to maintain a stick shape. Specifically, it should preferably have a rheometer hardness of 20 to 180, more preferably 40 to 140, as measured by a rheometer RT-2002D-D (Rheotech Co., Ltd., measurement terminal 3 mm diameter, penetration depth 10 mm, bench speed 5 cm/min, temperature 25° C., range 200 g).

EXAMPLES

Examples and Comparative Examples are shown below for further illustrating the invention although the invention is not limited thereto. Amounts are expressed in percent by weight (wt %) unless otherwise stated.

(1) Evaluation of Properties

The stick cosmetics of Examples and Comparative Examples were evaluated by a panel of ten members with respect to the following factors: stick breakage (collapse resistance of stick), feeling on use (unsticky feel), moisturizing effect (freshness), emollient effect (retention of moisturizing effect), spread (extension), formulation stability during 50° C./1 month storage, and ease of filling in a stick container (flow at elevated temperature). Each factor was evaluated according to the point table shown in Table 1. Based on an average of points of ten panel members, the result is rated according to the following judgment criteria. The results are shown in Tables.

TABLE 1

| Point | Breakage | Feeling on use | Moisturizing effect | Emollient effect | Spread | Storage stability |
|---|---|---|---|---|---|---|
| 5 | good | good | good | good | good | good |
| 4 | rather good | rather good | rather good | rather good | rather good | rather good |
| 3 | ordinary | ordinary | ordinary | ordinary | ordinary | ordinary |
| 2 | rather bad | rather bad | rather bad | rather bad | rather bad | rather bad |
| 1 | bad | bad | bad | bad | bad | bad |

TABLE 2

| Point | Ease of filling in stick container |
|---|---|
| 5 | good |
| 4 | rather good |
| 3 | ordinary |
| 2 | rather bad |
| 1 | bad |

(2) Judgment Criteria

⊚: average point≥4.5

◯: 3.5≤average point<4.5

Δ: 2.5≤average point<3.5

X: 1.5≤average point<2.5

X X: average point<1.5

Samples with ratings of Δ or better are considered passed.

Examples 1 to 6 and Comparative Examples 1 to 6

Stick-shaped cosmetic compositions of the following formulation were prepared and evaluated for the above properties.

TABLE 3

| | Component | Example 1 | 2 | 3 | 4 | 5 | 6 |
|---|---|---|---|---|---|---|---|
| 1 | (a) partially crosslinked polyether-modified silicone composition *1 | 5 | 2 | 2 | — | 2 | — |
| 2 | (a) partially crosslinked polyglycerol-modified silicone composition *2 | — | — | — | 2 | — | 2 |
| 3 | (d) alkyl-modified, partially crosslinked dimethylpolysiloxane composition *3 | — | 3 | 3 | 3 | 3 | 3 |
| 4 | phenyl-modified, partially crosslinked dimethylpolysiloxane composition *4 | — | — | — | — | — | — |
| 5 | (f) phenyl-modified silicone composite powder *5 | — | — | — | — | — | — |
| 6 | (e) PEG-9 polydimethylsiloxyethyl dimethicone *6 | — | — | 0.5 | 0.5 | 0.5 | — |
| 7 | (e) lauryl polyglyceryl-3 polydimethylsiloxyethyl dimethicone *7 | — | — | — | — | — | 0.5 |
| 8 | dimethylpolysiloxane *8 | 15.0 | 15.0 | 14.5 | 14.5 | 30.5 | 14.5 |
| 9 | diphenylsiloxyphenyl trimethicone *9 | 5 | 5 | 5 | 5 | 5 | 5 |
| 10 | (b) ceresin | 5 | 5 | 5 | 5 | 8 | 5 |
| 11 | (c) butylene glycol | 6 | 6 | 6 | 6 | 6 | 6 |
| 12 | (c) glycerol | 6 | 6 | 6 | 6 | 6 | 6 |
| 13 | sodium chloride | 1 | 1 | 1 | 1 | 1 | 1 |
| 14 | (c) water | 57 | 57 | 57 | 57 | 38 | 57 |
| | Total | 100 | 100 | 100 | 100 | 100 | 100 |
| Evaluation | Breakage | ◯ | ⊚ | ⊚ | ⊚ | ◯ | ⊚ |
| | Feeling on use | ◯ | ◯ | ◯ | ◯ | Δ | ◯ |
| | Moisturizing effect | ◯ | ◯ | ◯ | ◯ | Δ | ◯ |
| | Emollient effect | ◯ | ⊚ | ⊚ | ⊚ | ⊚ | ⊚ |
| | Spread | ⊚ | ⊚ | ⊚ | ⊚ | Δ | ⊚ |
| | Storage stability | Δ | ◯ | ⊚ | ◯ | ⊚ | ⊚ |

*1 partially crosslinked polyether-modified silicone composition (KSG-210, crosslinked portion 20-30%, dimethicone (6cs) 70-80%, Shin-Etsu Chemical Co. Ltd.)
*2 partially crosslinked polyglycerol-modified silicone composition (KSG-710, crosslinked portion 20-30%, dimethicone(6cs) 70-80%, Shin-Etsu Chemical Co. Ltd.)
*3 alkyl-modified, partially crosslinked dimethypolysiloxane composition (KSG-41A, crosslinked portion 20-30%, mineral oil 70-80%, Shin-Etsu Chemical Co. Ltd.)
*4 phenyl-modified, partially crosslinked dimethylpolysiloxane composition (KSG-18A, crosslinked portion 10-20%, diphenylsiloxyphenyl trimethicone 80-90%, Shin-Etsu Chemical Co., Ltd.)
*5 phenyl-modified silicone composite powder (KSP-300, average primary particle size 5 μm, spherical particles, Shin-Etsu Chemical Co., Ltd.)
*6 PEG-9 polydimethylsiloxyethyl dimethicone (KF-6028, Shin-Etsu Chemical Co., Ltd.)
*7 lauryl polyglyceryl-3 polydimethylsiloxyethyl dimethicone (KF-6105, Shin-Etsu Chemical Co., Ltd.)
*8 dimethylpolsiloxane (KF-96A-6cs, Shin-Etsu Chemical Co., Ltd.)
*9 diphenylsiloxyphenyl trimethicone (KF-56A, Shin-Etsu Chemical Co., Ltd.)

The amounts in the Table are amounts blended in the formulated product (the same holds true, hereinafter).

good in feeling on use (unsticky feel), moisturizing effect (freshness), emollient effect (retention of moisturizing effect), spread (extension), and storage stability.

As seen from Table 4, Comparative Examples 1 to 3 using silicone elastomer instead of component (a) according to the invention, Comparative Example 4 using a small amount of component (C), and Comparative Example 5 using less swelling elastomer as the elastomer in component (d) fail to achieve satisfactory properties. Comparative Example 6 not containing component (b) cannot be shaped into a stick.

Examples 7 to 9

The stick-shaped cosmetic compositions formulated as shown in Table 5 were prepared and evaluated for the properties.

TABLE 4

| | | Comparative Example | | | | | |
|---|---|---|---|---|---|---|---|
| | Component | 1 | 2 | 3 | 4 | 5 | 6 |
| 1 | (a) partially crosslinked polyether-modified silicone composition *1 | — | — | — | 2 | — | 2 |
| 2 | (a) partially crosslinked polyglycerol-modified silicone composition *2 | — | — | — | — | — | — |
| 3 | (d) alkyl-modified, partially crosslinked dimethylpolysiloxane composition *3 | 5 | 5 | — | 3 | — | 3 |
| 4 | phenyl-modified, partially crosslinked dimethylpolysiloxane composition *4 | — | — | 5 | — | — | — |
| 5 | (f) phenyl-modified silicone composite powder *5 | — | — | — | — | 3 | — |
| 6 | (e) PEG-9 polydimethylsiloxyethyl dimethicone *6 | 0.5 | 2 | 2 | 0.5 | 2 | 0.5 |
| 7 | (e) lauryl polyglyceryl-3 polydimethylsiloxyethyl dimethicone *7 | — | — | — | — | — | — |
| 8 | dimethylpolysiloxane *8 | 14.5 | 13.0 | 13.0 | 49.5 | 15.0 | 19.5 |
| 9 | diphenylsiloxyphenyl trimethicone *9 | 5 | 5 | 5 | 5 | 5 | 5 |
| 10 | (b) ceresin | 5 | 5 | 5 | 10 | 5 | — |
| 11 | (c) butylene glycol | 6 | 6 | 6 | 6 | 6 | 6 |
| 12 | (c) glycerol | 6 | 6 | 6 | 6 | 6 | 6 |
| 13 | sodium chloride | 1 | 1 | 1 | 1 | 1 | 1 |
| 14 | (c) water | 57 | 57 | 57 | 17 | 57 | 57 |
| | Total | 100 | 100 | 100 | 100 | 100 | 100 |
| Evaluation | Breakage | X | X | X | ○ | X | — |
| | Feeling on use | Δ | X | X | X | Δ | — |
| | Moisturizing effect | X | X | X | X | X | — |
| | Emollient effect | ◎ | ◎ | Δ | ○ | X | — |
| | Spread | ○ | ○ | ○ | X | ○ | — |
| | Storage stability | X X | X | X | Δ | X | — |

<Preparation of Cosmetic Composition>
The cosmetic composition was prepared by
step A of heating components (1) to (9) at 90° C. and mixing them until uniform,
step B of mixing components (11) to (14) until uniform and heating the mixture at 85° C., and
step C of adding B to A, emulsifying, filling the emulsion in a stick container, and slowly cooling.

As seen from Table 3, the stick-shaped cosmetic compositions of Examples 1 to 6 avoid breakage of stick, and are

TABLE 5

| | | Example | | |
|---|---|---|---|---|
| | Component | 7 | 8 | 9 |
| 1 | (a) partially crosslinked polyether-modified silicone composition *1 | 3 | 3 | 3 |
| 2 | (d) alkyl-modified, partially crosslinked dimethylpolysiloxane composition *3 | 5 | — | — |

TABLE 5-continued

| | | Example | | |
|---|---|---|---|---|
| | Component | 7 | 8 | 9 |
| 3 | phenyl-modified, partially crosslinked dimethylpolysiloxane composition *4 | — | 5 | — |
| 4 | partially crosslinked dimethylpolysiloxane composition *10 | — | — | 5 |

TABLE 5-continued

|   | Component | Example 7 | Example 8 | Example 9 |
|---|---|---|---|---|
| 5 | (e) PEG-9 polydimethylsiloxyethyl dimethicone *6 | 0.5 | 0.5 | 0.5 |
| 6 | dimethylpolysiloxane *8 | 16.5 | 16.5 | 16.5 |
| 7 | (b) ceresin | 5 | 5 | 5 |
| 8 | (c) butylene glycol | 6 | 6 | 6 |
| 9 | (c) glycerol | 6 | 6 | 6 |
| 10 | sodium chloride | 1 | 1 | 1 |
| 11 | (c) water | 57 | 57 | 57 |
|   | Total | 100 | 100 | 100 |
|   | Evaluation Ease of filling in stick container | ⊚ | Δ | Δ |
|   | Feeling on use | ○ | ○ | ○ |

*10 partially crosslinked dimethylpolysiloxane composition (KSG-16, crosslinked portion 20-30%, dimethicone (6cs) 70-80%, Shin-Etsu Chemical Co., Ltd.)

<Preparation of Cosmetic Composition>
The cosmetic composition was prepared by
step A of heating components (1) to (7) at 90° C. and mixing them until uniform,
step B of mixing components (8) to (11) until uniform and heating the mixture at 85° C., and
step C of adding B to A, emulsifying, filling the emulsion in a stick container, and slowly cooling.

As seen from Table 5, the stick-shaped cosmetic composition of Example 7 having component (d) blended therein was smoothly flowing at high temperature and thus easy to fill in a stick container.

Examples 10 and 11

The stick-shaped cosmetic compositions formulated as shown in Table 6 were prepared and evaluated for the properties.

TABLE 6

|   | Component | Example 10 | Example 11 |
|---|---|---|---|
| 1 | (a) partially crosslinked polyether-modified silicone composition *1 | 3.5 | 3.5 |
| 2 | (d) alkyl-modified, partially crosslinked dimethylpolysiloxane composition *11 | 3 | 3 |
| 3 | PEG-10 dimethicone *12 | 0.5 | 0.5 |
| 4 | decamethylcyclopentasiloxane *13 | 19 | 19 |
| 5 | triethylhexanoin | 1 | 1 |
| 6 | (b) ceresin | 5 | 5 |
| 7 | (f) phenyl-modified silicone composite powder *5 | — | 2 |
| 8 | (c) butylene glycol | 6 | 6 |
| 9 | (c) glycerol | 5.5 | 5.5 |
| 10 | sodium chloride | 1 | 1 |
| 11 | sodium citrate | 0.2 | 0.2 |
| 12 | methyl paraben | 0.2 | 0.2 |
| 13 | (c) water | 55.1 | 53.1 |
|   | Total | 100 | 100 |
|   | Evaluation Moisturizing effect | ○ | ⊚ |
|   | Feeling on use | ○ | ⊚ |

*11 alkyl-modified, partially crosslinked dimethylpolysiloxane composition (KSG-43, crosslinked portion 25-35%, triethylhexanoin 65-75%, Shin-Etsu Chemical Co., Ltd.)
*12 PEG-10 dimethicone (KF-6017, Shin-Etsu Chemical Co., Ltd.)
*13 decamethylcyclopentasiloxane (KF-995, Shin-Etsu Chemical Co., Ltd.)

<Preparation of Cosmetic Composition>
The cosmetic composition was prepared by
step A of heating components (1) to (7) at 90° C. and mixing them until uniform,
step B of mixing components (8) to (12) until uniform and heating the mixture at 85° C., and
step C of adding B to A, emulsifying, filling the emulsion in a stick container, and slowly cooling.

As seen from Table 6, the stick-shaped cosmetic composition of Example 11 having powder (f) blended therein gives a fresh feeling on use. Since powder (f) suppresses stickiness inherent to wax, the composition gives a pleasant feeling on use.

Example 12

W/O moisture stick
<Preparation of Cosmetic Composition>
The cosmetic composition was prepared by
step A of heating components (1) to (8) at 95° C. and mixing them until uniform,
step B of mixing components (9) to (16) until uniform and heating the mixture at 85° C., and
step C of adding B to A, emulsifying, filling the emulsion in a stick container, and slowly cooling.

| 1. Alkyl-modified, partially crosslinked polyglycerol-modified silicone composition *14 | 4 |
|---|---|
| 2. Alkyl-modified, partially crosslinked dimethylpolysiloxane composition *11 | 3 |
| 3. Lauryl PEG-9 polydimethylsiloxyethyl dimethicone *15 | 0.6 |
| 4. Squalane | 17.8 |
| 5. Jojoba oil | 1 |
| 6. Tocopherol | 0.1 |
| 7. Polyethylene | 6 |
| 8. Beeswax | 0.5 |
| 9. Pentylene glycol | 3 |
| 10. Glycerol | 12 |
| 11. Sorbitol (70% solution) | 5 |
| 12. Xanthane gum | 0.05 |
| 13. Sodium chloride | 1 |
| 14. Sodium citrate | 0.2 |
| 15. Phenoxyethanol | 0.3 |
| 16. Water | balance |
| Total | 100.0 |

*14 Alkyl-modified, partially crosslinked polyglycerol-modified silicone composition (KSG-840, crosslinked portion 25-35%, squalane 65-75%, Shin-Etsu Chemical Co., Ltd.)
*15 Lauryl PEG-9 polydimethylsiloxyethyl dimethicone (KF-6038, Shin-Etsu Chemical Co., Ltd.)

The resulting W/O moisture stick was good in feeling on use, moisturizing effect, emollient effect, spread, and formulation stability.

Example 13

W/O body stick
<Preparation of Cosmetic Composition>
The cosmetic composition was prepared by
step A of heating components (1) to (8) at 85° C. and mixing them at 80° C. until uniform,
step B of mixing components (9) to (14) until uniform and heating the mixture at 70° C., and
step C of adding B to A, emulsifying, filling the emulsion in a stick container, and slowly cooling.

| 1. Partially crosslinked polyether-modified silicone composition *1 | 3.5 |
|---|---|
| 2. Silicone alkyl-modified, partially crosslinked dimethylpolysiloxane composition *16 | 3 |
| 3. PEG-9 polydimethylsiloxyethyl dimethicone *6 | 0.5 |
| 4. Decamethylcyclopentasiloxane *13 | 4 |
| 5. Trimethyl trimethicone *17 | 4 |
| 6. Diphenylsiloxyphenyl trimethicone *9 | 4 |
| 7. Polymethylsilsesquioxane *18 | 2 |
| 8. Ceresin | 6 |

-continued

| | |
|---|---|
| 9. Dipropylene glycol | 8 |
| 10. Ethanol | 4 |
| 11. Sodium chloride | 1 |
| 12. Sodium citrate | 0.2 |
| 13. Methyl paraben | 0.2 |
| 14. Water | balance |
| Total | 100.0 |

*16 Silicone alkyl-modified, partially crosslinked dimethylpolysiloxane composition (KSG-045Z, crosslinked portion 15-25%, cyclopentasiloxane 75-85%, Shin-Etsu Chemical Co., Ltd.)
*17 Trimethyl trimethicone (TMF-1.5, Shin-Etsu Chemical Co., Ltd.)
*18 Polymethylsilsesquioxane (KMP-590, Shin-Etsu Chemical Co., Ltd.)

The resulting W/O body stick was good in feeling on use, moisturizing effect, emollient effect, spread, and formulation stability.

Example 14

W/O base stick

<Preparation of Cosmetic Composition>

The cosmetic composition was prepared by step A of milling components (11) to (16) on a three roll mill to form a paste, step B of heating A and components (1) to (10) at 95° C. and mixing them until uniform, step C of mixing components (17) to (22) until uniform and heating the mixture at 85° C., and step D of adding C to B, emulsifying, filling the emulsion in a stick container, and slowly cooling.

| | |
|---|---|
| 1. Alkyl-modified, partially crosslinked polyether-modified silicone composition *19 | 3.5 |
| 2. Alkyl-modified, partially crosslinked dimethylpolysiloxane composition *11 | 3 |
| 3. Lauryl PEG-9 polydimethylsiloxyethyl dimethicone *15 | 0.5 |
| 4. Decamethylcyclopentasiloxane *13 | 10 |
| 5. Diphenylsiloxyphenyl trimethicone *9 | 5 |
| 6. Ethylhexyl methoxycinnamate | 1 |
| 7. Silicone composite powder *20 | 2 |
| 8. Acrylic silicone base graft copolymer *21 | 1 |
| 9. Polyethylene | 3 |
| 10. Paraffin | 3 |
| 11. Isotridecyl isononanoate | 1.8 |
| 12. Silicone branched polyglycerol-modified silicone *22 | 0.2 |
| 13. Silicone-treated titanium oxide *23 | 1.7 |
| 14. Silicone-treated yellow iron oxide *23 | 0.2 |
| 15. Silicone-treated red iron oxide *23 | 0.08 |
| 16. Silicone-treated black iron oxide *23 | 0.02 |
| 17. Butylene glycol | 8 |
| 18. PEG-32 | 4 |
| 19. Sodium chloride | 1 |
| 20. Sodium citrate | 0.2 |
| 21. Methyl paraben | 0.2 |
| 22. Water | balance |
| Total | 100.0 |

*19 Alkyl-modified, partially crosslinked polyether-modified silicone composition (KSG-310, crosslinked portion 25-35%, mineral oil 65-75%, Shin-Etsu Chemical Co., Ltd.)
*20 Silicone composite powder (KSP-105, Shin-Etsu Chemical Co., Ltd.)
*21 Acrylic silicone base graft copolymer (KP-545, Shin-Etsu Chemical Co., Ltd.)
*22 Silicone branched polyglycerol-modified silicone (KF-6106, Shin-Etsu Chemical Co., Ltd.)
*23 Silicone-treated powders (titanium oxide, yellow iron oxide, red iron oxide, and black iron oxide surface-treated with KF-9909 (Shin-Etsu Chemical Co., Ltd.) to be hydrophobic)

The resulting W/O base stick was good in feeling on use, long-lasting performance, moisturizing effect, emollient effect, spread, and formulation stability.

Example 15

W/O stick concealer

<Preparation of Cosmetic Composition>

The cosmetic composition was prepared by step A of heating components (1) to (10) at 95° C. and mixing them until uniform, step B of mixing components (11) to (17) until uniform and heating the mixture at 85° C., and step C of adding B to A, emulsifying, filling the emulsion in a stick container, and slowly cooling.

| | |
|---|---|
| 1. Partially crosslinked polyether-modified silicone composition *1 | 3.5 |
| 2. Alkyl-modified, partially crosslinked dimethylpolysiloxane composition *11 | 1 |
| 3. Partially crosslinked dimethylpolysiloxane composition *24 | 2 |
| 4. PEG-9 polydimethylsiloxyethyl dimethicone *6 | 0.5 |
| 5. Dimethylpolysiloxane *8 | 10 |
| 6. Triethylhexanoin | 8 |
| 7. Synthetic wax | 6 |
| 8. Silicone wax *25 | 0.5 |
| 9. Phenyl-modified silicone composite powder *5 | 3 |
| 10. Silicone composite powder *20 | 2 |
| 11. Dipropylene glycol | 6 |
| 12. Glycerol | 2 |
| 13. Trehalose | 2 |
| 14. Sodium chloride | 1 |
| 15. Sodium citrate | 0.2 |
| 16. Methyl paraben | 0.2 |
| 17. Water | balance |
| Total | 100.0 |

*24 Partially crosslinked dimethylpolysiloxane composition (KSG-19, crosslinked portion 10-20%, dimethicone (6cs) 80-90%, Shin-Etsu Chemical Co., Ltd.)
*25 Silicone wax (KP-561P, Shin-Etsu Chemical Co., Ltd.)

The resulting W/O stick concealer was good in feeling on use, wrinkle-concealing effect, moisturizing effect, emollient effect, spread, and formulation stability.

Example 16

W/O stick concealer

<Preparation of Cosmetic Composition>

The cosmetic composition was prepared by step A of heating components (1) to (10) at 95° C. and mixing them until uniform, step B of mixing components (11) to (17) until uniform and heating the mixture at 85° C., and step C of adding B to A, emulsifying, filling the emulsion in a stick container, and slowly cooling.

| | |
|---|---|
| 1. Partially crosslinked polyether-modified silicone composition *1 | 3.5 |
| 2. Alkyl-modified, partially crosslinked dimethylpolysiloxane composition *11 | 1.5 |
| 3. Partially crosslinked dimethylpolysiloxane composition *24 | 2 |
| 4. PEG-9 polydimethylsiloxyethyl dimethicone *6 | 0.5 |
| 5. Dimethylpolysiloxane *8 | 14 |
| 6. Triethylhexanoin | 12 |
| 7. Synthetic wax | 7.5 |
| 8. Silicone wax *25 | 0.5 |
| 9. Phenyl-modified silicone composite powder *5 | 3 |
| 10. Silicone composite powder *20 | 2 |
| 11. Dipropylene glycol | 6 |
| 12. Glycerol | 2 |
| 13. Trehalose | 2 |

-continued

| | |
|---|---|
| 14. Sodium chloride | 1 |
| 15. Sodium citrate | 0.2 |
| 16. Methyl paraben | 0.2 |
| 17. Water | balance |
| Total | 100.0 |

The resulting W/O stick concealer was good in feeling on use, wrinkle-concealing effect, moisturizing effect, emollient effect, spread, and formulation stability.

Example 17

W/O stick concealer
<Preparation of Cosmetic Composition>
The cosmetic composition was prepared by
step A of heating components (1) to (10) at 95° C. and mixing them until uniform,
step B of mixing components (11) to (17) until uniform and heating the mixture at 85° C., and
step C of adding B to A, emulsifying, filling the emulsion in a stick container, and slowly cooling.

| | |
|---|---|
| 1. Partially crosslinked polyether-modified silicone composition *1 | 3.5 |
| 2. Alkyl-modified, partially crosslinked dimethylpolysiloxane composition *11 | 2 |
| 3. Partially crosslinked dimethylpolysiloxane composition *24 | 2 |
| 4. PEG-9 polydimethylsiloxyethyl dimethicone *6 | 0.5 |
| 5. Dimethylpolysiloxane *8 | 18 |
| 6. Triethylhexanoin | 16 |
| 7. Synthetic wax | 9 |
| 8. Silicone wax *25 | 0.5 |
| 9. Phenyl-modified silicone composite powder *5 | 3 |
| 10. Silicone composite powder *20 | 2 |
| 11. Dipropylene glycol | 6 |
| 12. Glycerol | 2 |
| 13. Trehalose | 2 |
| 14. Sodium chloride | 1 |
| 15. Sodium citrate | 0.2 |
| 16. Methyl paraben | 0.2 |
| 17. Water | balance |
| Total | 100.0 |

The resulting W/O stick concealer was good in feeling on use, wrinkle-concealing effect, moisturizing effect, emollient effect, spread, and formulation stability.

Example 18

W/O moisture stick
<Preparation of Cosmetic Composition>
The cosmetic composition was prepared by
step A of heating components (1) to (6) at 90° C. and mixing them until uniform,
step B of mixing components (7) to (12) until uniform and heating the mixture at 85° C., and
step C of adding B to A, emulsifying, filling the emulsion in a stick container, and slowly cooling.

| | |
|---|---|
| 1. Partially crosslinked polyglycerol-modified silicone composition *2 | 3.5 |
| 2. Alkyl-modified, partially crosslinked dimethylpolysiloxane composition *11 | 3.5 |
| 3. Silicone branched polyglycerol-modified silicone *22 | 0.8 |
| 4. Dimethylpolysiloxane *8 | 10 |
| 5. Triethylhexanoin | 10 |
| 6. Ceresin | 6 |
| 7. Butylene glycol | 8.5 |
| 8. Glycerol | 6 |
| 9. Sodium chloride | 1 |
| 10. Sodium citrate | 0.2 |
| 11. Methyl paraben | 0.1 |
| 12. Water | balance |
| Total | 100.0 |

The resulting W/O moisturizing stick was good in feeling on use, moisturizing effect, emollient effect, spread, and formulation stability.

Example 19

W/O stick foundation
<Preparation of Cosmetic Composition>
The cosmetic composition was prepared by
step A of milling components (7) to (13) on a three roll mill to form a paste,
step B of heating A and components (1) to (6) at 90° C. and mixing them until uniform,
step C of mixing components (14) to (19) until uniform and heating the mixture at 85° C., and
step D of adding C to B, emulsifying, filling the emulsion in a stick container, and slowly cooling.

| | |
|---|---|
| 1. Partially crosslinked polyglycerol-modified silicone composition *2 | 3.5 |
| 2. Alkyl-modified, partially crosslinked dimethylpolysiloxane composition *11 | 3.5 |
| 3. Silicone branched polyglycerol-modified silicone *22 | 1.8 |
| 4. Dimethylpolysiloxane *8 | 12 |
| 5. Diphenylsiloxyphenyl trimethicone *9 | 10 |
| 6. Ceresin | 6 |
| 7. Isotridecyl isononanoate | 3.5 |
| 8. Silicone branched polyglycerol-modified Silicone *22 | 0.2 |
| 9. Silicone-treated titanium oxide *23 | 6.5 |
| 10. Silicone-treated talc *26 | 0.6 |
| 11. Silicone-treated yellow iron oxide *23 | 0.75 |
| 12. Silicone-treated red iron oxide *23 | 0.14 |
| 13. Silicone-treated black iron oxide *23 | 0.01 |
| 14. Butylene glycol | 8.5 |
| 15. Glycerol | 6 |
| 16. Sodium chloride | 1 |
| 17. Sodium citrate | 0.2 |
| 18. Methyl paraben | 0.1 |
| 19. Water | balance |
| Total | 100.0 |

*26 Silicone-treated powder (talc surface-treated with KF-9909 (Shin-Etsu Chemical Co., Ltd.) to be hydrophobic)

The resulting W/O stick foundation was good in feeling on use, moisturizing effect, emollient effect, spread, and formulation stability.

The invention claimed is:
1. A stick-shaped cosmetic composition consisting of:
(a) 0.1 to 4% by weight of at least one member selected from a partially crosslinked polyether-modified silicone and a partially crosslinked polyglycerol-modified silicone;
(b) 1 to 10% by weight of a wax;
(c) at least 60% by weight of an aqueous component;
(d) 0.1 to 4% by weight of a partially crosslinked organopolysiloxane having an alkyl branched chain in its backbone, exclusive of component (a), and

(e) 0.1 to 0.8% by weight of a non-crosslinked silicone active agent, optionally with any of:

(f) silicone powder, (1) oil selected from the group of consisting of dimethylpolysiloxane, cyclopentasiloxane, cyclohexasiloxane, disiloxane, trisiloxane, methyl trimethicone, caprylyl methicone, methylphenylpolysiloxane, methylhexylpolysiloxane, methylhydrogenpolysiloxane, dimethylsiloxane/methylphenylsiloxane copolymers, amino-modified organopolysiloxane, pyrrolidone-modified organopolysiloxane, pyrrolidonecarboxylic acid-modified organopolysiloxane, gum-like dimethylpolysiloxane having a high degree of polymerization, gum-like amino-modified organopolysiloxane, gum-like dimethylsiloxane/methylphenylsiloxane copolymers, cyclic organopolysiloxane solution of silicone gum or rubber, trimethylsiloxysilicic acid, cyclic siloxane solution of trimethylsiloxysilicid acid, higher alkoxy-modified silicone, higher fatty acid-modified silicone, alkyl-modified silicone, long chain alkyl-modified silicone, amino acid-modified silicone, fluorine-modified silicone, natural animal and vegetable oils and fats, semi-synthetic oils and fats, hydrocarbon oils, higher alcohols, fatty acids, ester oils, and fluorochemical oils, (2) powder other than component (f), (3) composition consisting of a crosslinked organopolysiloxane and an oil which is liquid at room temperature, (4) film-forming agent selected from the group of consisting of latexes, cellulose derivatives, silicone-modified polysaccharides, acrylic silicone base graft copolymers, trimethylsiloxysilicic acid, silicone-modified polynorbornene, fluorine-modified silicone resins, fluoro-resins, aromatic hydrocarbon resins, polymer emulsion resins, terpene resins, polybutene, polyisoprene, alkyd resins, polyvinyl pyrrolidone-modified polymers, rosin-modified resins, and polyurethane, (5) surfactant other than component (a) and (e), and (6) oil-soluble gelling agents, antiperspirants, UV absorbers, moisturizers, preservatives, bactericides, perfumes, salts, antioxidants, pH adjusting agents, chelating agents, refreshing agents, anti-inflammatory agents, brightening agent, cell activating agent, anti-skin-roughening agent, blood flow promotor, skin astringent, antiseborrheic agent, vitamins, amino acids, water-soluble polymers, and inclusion compounds.

2. The stick-shaped cosmetic composition of claim 1, wherein an amount of the component (f) is 0.1 to 5% by weight.

3. The stick-shaped cosmetic composition of claim 1, wherein the component (c) consists of water and at least one component selected from the group consisting of moisturizers, humectants and mixtures thereof.

4. The stick-shaped cosmetic composition of claim 1, wherein the component (c) consists of water and at least one component selected from the group consisting of lower alcohols, sugar alcohols, polyhydric alcohols, glucose, glyceryl glucoside, betaine, hyaluronic acid, chondroitin sulfate, pyrrolidone carboxylate, polyoxyethylene methyl glucoside, polyoxypropylene methyl glucoside and mixtures thereof.

5. The stick-shaped cosmetic composition of claim 1, wherein the component (c) consists of water, butylene glycol, and glycerol.

6. The stick-shaped cosmetic composition of claim 1, wherein the amount of component (c) is 60 to 90% by weight of the total weight of the composition.

7. The stick-shaped cosmetic composition of claim 1, wherein the amount of component (d) is 0.2 to 2% by weight of the total weight of the composition.

8. A stick-shaped cosmetic composition consisting of:
(a) 0.1 to 4% by weight of at least one member selected from a partially crosslinked polyether-modified silicone and a partially crosslinked polyglycerol-modified silicone;
(b) 1 to 10% by weight of a wax;
(c) at least 60% by weight of an aqueous component;
(d) 0.1 to 4% by weight of a partially crosslinked organopolysiloxane having an alkyl branched chain in its backbone, exclusive of component (a);
(e) 0.1 to 0.8% by weight of a non-crosslinked silicone active agent; and
(g) film-forming agent selected from the group of consisting of latexes, cellulose derivatives, silicone-modified polysaccharides, acrylic silicone base graft copolymers, trimethylsiloxysilicic acid, silicone-modified polynorbornene, fluorine-modified silicone resins, fluoro-resins, aromatic hydrocarbon resins, polymer emulsion resins, terpene resins, polybutene, polyisoprene, alkyd resins, polyvinyl pyrrolidone-modified polymers, rosin-modified resins, and polyurethane.

9. A stick-shaped cosmetic composition consisting of:
(a) 0.1 to 4% by weight of at least one member selected from a partially crosslinked polyether-modified silicone and a partially crosslinked polyglycerol-modified silicone;
(b) 1 to 10% by weight of a wax;
(c) at least 60% by weight of an aqueous component;
(d) 0.1 to 4% by weight of a partially crosslinked organopolysiloxane having an alkyl branched chain in its backbone, exclusive of component (a);
(e) 0.1 to 0.8% by weight of a non-crosslinked silicone active agent, and at least one component selected from:
(f) silicone powder;
(1) oil selected from the group of consisting of dimethylpolysiloxane, cyclopentasiloxane, cyclohexasiloxane, disiloxane, trisiloxane, methyl trimethicone, caprylyl methicone, methylphenylpolysiloxane, methylhexylpolysiloxane, methylhydrogenpolysiloxane, dimethylsiloxane/methylphenylsiloxane copolymers, amino-modified organopolysiloxane, pyrrolidone-modified organopolysiloxane, pyrrolidonecarboxylic acid-modified organopolysiloxane, gum-like dimethylpolysiloxane having a high degree of polymerization, gum-like amino-modified organopolysiloxane, gum-like dimethylsiloxane/methylphenylsiloxane copolymers, cyclic organopolysiloxane solution of silicone gum or rubber, trimethylsiloxysilicic acid, cyclic siloxane solution of trimethylsiloxysilicid acid, higher alkoxy-modified silicone, higher fatty acid-modified silicone, alkyl-modified silicone, long chain alkyl-modified silicone, amino acid-modified silicone, fluorine-modified silicone, natural animal and vegetable oils and fats, semi-synthetic oils and fats, hydrocarbon oils, higher alcohols, fatty acids, ester oils, and fluorochemical oils;
(2) powder other than component (f);
(3) composition consisting of a crosslinked organopolysiloxane and an oil which is liquid at room temperature;
(4) film-forming agent selected from the group of consisting of latexes, cellulose derivatives, silicone-modified polysaccharides, acrylic silicone base graft copolymers, trimethylsiloxysilicic acid, silicone-modified polynorbornene, fluorine-modified silicone resins, fluoro-resins, aromatic hydrocarbon resins, polymer emulsion resins, terpene resins, polybutene, polyisoprene, alkyd resins, polyvinyl pyrrolidone-modified polymers, rosin-modified resins, and polyurethane;

(5) surfactant other than component (a) and (e); and (6) oil-soluble gelling agents, antiperspirants, UV absorbers, moisturizers, preservatives, bactericides, perfumes, salts, antioxidants, pH adjusting agents, chelating agents, refreshing agents, anti-inflammatory agents, brightening agent, cell activating agent, anti-skin-roughening agent, blood flow promotor, skin astringent, antiseborrheic agent, vitamins, amino acids, water-soluble polymers, and inclusion compounds.

* * * * *